United States Patent
Sogan et al.

(10) Patent No.: US 7,468,790 B2
(45) Date of Patent: Dec. 23, 2008

(54) DETECTING GASEOUS SPECIES BY LIGHT-EMISSION SPECTROMETRY WITH SPECTRUM PROCESSING

(75) Inventors: Gloria Sogan, Epagny (FR); Julien Bounouar, Annecy-le-Vieux (FR); Jean-Pierre Desbiolles, Cruseilles (FR); Isabelle Gaurand, Annecy le Vieux (FR)

(73) Assignee: Alcatel, Paris (FR)

( * ) Notice: Subject to any disclaimer, the term of this patent is extended or adjusted under 35 U.S.C. 154(b) by 314 days.

(21) Appl. No.: 11/064,483

(22) Filed: Feb. 24, 2005

(65) Prior Publication Data

US 2005/0190363 A1 Sep. 1, 2005

(30) Foreign Application Priority Data

Feb. 26, 2004 (FR) .................................. 04 50354

(51) Int. Cl.
*C23C 16/00* (2006.01)
*G01J 3/30* (2006.01)
(52) U.S. Cl. ........................................... 356/301; 438/9
(58) Field of Classification Search ........................ None
See application file for complete search history.

(56) References Cited

U.S. PATENT DOCUMENTS

| | | | |
|---|---|---|---|
| 3,836,255 A * | 9/1974 | Schuman | ..................... 356/311 |
| 5,014,217 A | 5/1991 | Savage | |
| 5,658,423 A | 8/1997 | Angell et al. | |
| 5,706,082 A * | 1/1998 | Colgan et al. | ................ 356/311 |
| 5,991,020 A | 11/1999 | Loge | |
| 6,046,796 A | 4/2000 | Markle et al. | |
| 6,101,971 A * | 8/2000 | Denholm et al. | ......... 118/723 E |
| 6,157,867 A | 12/2000 | Hwang et al. | |

FOREIGN PATENT DOCUMENTS

| | | |
|---|---|---|
| EP | 0 584 676 A | 3/1994 |
| EP | 0 677 737 A2 | 10/1995 |
| WO | WO 02/44698 A | 6/2002 |

OTHER PUBLICATIONS

U.S. Appl. No. 11/064,484, filed Feb. 24, 2005, entitled "Detecting Minority Gaseous Species by Light-Emission Spectroscopy."

* cited by examiner

*Primary Examiner*—L. G. Lauchman
*Assistant Examiner*—Rebecca C Slomski
(74) *Attorney, Agent, or Firm*—Sughrue Mion, PLLC

(57) ABSTRACT

A method of detecting gaseous species in a mixture by light-emission spectroscopy, in which use is made of the radiation emitted by a plasma (4) present in the gas mixture under analysis, a measurement system (20) is used to take a raw optical spectrum of said radiation emitted by the plasma (4), and the raw optical spectrum is compared with a library of reference optical spectra, the method comprising a step of generating a pruned optical spectrum, which step consists in making use, in the raw optical spectrum, of only those zones of the spectrum that present a significant shape corresponding to a predefined shape criterion, and subsequently said pruned spectrum is compared with the library of reference optical spectra.

13 Claims, 5 Drawing Sheets

RELATED ART

DETECTING GASEOUS SPECIES BY LIGHT-EMISSION SPECTROMETRY WITH SPECTRUM PROCESSING

BACKGROUND OF THE INVENTION

The present invention relates to detecting gaseous species in a mixture by light-emission spectroscopy.

In order to detect gaseous species, recourse has already been made to light-emission spectroscopy, in which use is made of the light radiation emitted by a plasma present in the gas mixture for analysis, the optical spectrum of said radiation emitted by the plasma is measured, and the optical spectrum is analyzed in order to deduce therefrom the presence of gaseous species in the mixture.

The conventional method used for the step of analyzing the optical spectrum consists in viewing the optical spectrum in real time and in comparing it with spectra published in scientific libraries and established for each gaseous species. The method relies on the fact that each gaseous species generates light radiation of spectrum that is characteristic when it reaches a level of excitation causing it to emit light. Scientific libraries thus contain the light-emission spectra for each gaseous species. Each spectrum is constituted by a curve plotting light intensity values as a function of wavelength over the wavelength range constituting light radiation, i.e. in the ultraviolet, in the visible spectrum, and in the infrared. Generally, the light-emission spectrum of a gaseous species is a jagged curve presenting a large number of peaks or "lines". Each line is characterized by the wavelength and by the intensity of the light radiation and/or wavelength.

In known apparatuses, the light-emission spectrum is generally viewed by means of a computer which scans through the data issued by an optical spectrometer. Software associated with the spectrometer usually makes it possible to act on the integration time of the signal coming from the spectrometer, and thus on the intensity of the spectrum. The software may also act on the number of spectra to be averaged prior to display, thus making it possible to reduce noise. The software then allows the instantaneous light-emission spectrum to be viewed, and allows the variation in the amplitude of certain lines to be tracked, in order to deduce changes in the presence of a gas. The amplitude of a line A1 at wavelength $\lambda 1$ from a measurement spectrum associated with identifying a species A makes it possible, when the gas is on its own, to monitor variation in the presence of that gas. The software also makes it possible to perform a certain number of mathematical operations such as subtracting spectra.

However, the drawback of those traditional techniques lies in the difficulty of interpreting the resulting spectrum. It is not possible to determine immediately the or each species contained in a mixture. That makes it necessary to consult tables of known spectra and to attempt to recognize the lines of known spectra in the spectrum under analysis. A first line is identified in the spectrum of the literature, then a second, . . . .

Spectrum analysis needs to be performed by an expert, since there are numerous difficulties, and in particular:

in the spectrum under analysis, some of the lines of the gaseous species being sought can be missing, even though the gaseous species is genuinely present; certain lines can be missing as the result, in particular, of the conditions under which the plasma is generated, since the presence of these lines depends on the power of the plasma and on other parameters of the plasma;

in the spectrum under analysis, because the spectrometer is necessarily of limited resolution, it is often difficult to know accurately the characteristic wavelength of a spectrum line, which then makes it difficult to allocate the line to one or another of a plurality of possible gaseous species; this becomes particularly difficult in the presence of lines that are very close together;

certain gaseous species that are easily excited can block out other gases of interest from the display since they do not have enough energy to reach excitation levels at which they emit light; as a result, some or all of the lines of a gaseous species can be missing because of the presence of other gaseous species that are easily excited, and this needs to be taken into account when analyzing the spectrum; and the software associated with the spectrometer is not capable of reliably interpreting variation in the amplitude of radiation at the characteristic wavelengths of the spectrum; for example, in the presence of a first species A presenting a line A1 of wavelength $\lambda 1$ as shown in FIG. 3A, the software will track variation in the amplitude at the wavelength $\lambda 1$; if a second species B is then introduced into the mixture, where said second species has a line B1 at wavelength $\lambda 2$ close to $\lambda 1$, as shown in FIG. 3B, then the software will detect an increase in the amplitude of A1 up to A1' and runs the risk of detecting an increase in the quantity of the species A, as shown in FIG. 3C, whereas, in fact, it is the presence of the species B that explains the increase in the amplitude at wavelength $\lambda 1$; this shows that it is unsafe to follow variation of a species on the basis of the amplitude of a single line; and a plurality of tracked lines are even more complicated to interpret.

The expert needs to take all of the above difficulties into account in order to extract from the resulting spectrum information that is pertinent about the presence of the various gaseous species in the mixture and how they vary.

Those traditional solutions thus require permanent intervention by an expert in order to analyze the spectra that are obtained, and such analysis is lengthy and tedious, making it inconceivable to perform analysis in real time, e.g. for the purpose of detecting real-time variation in a parameter of the equipment through which the gas mixture under analysis is flowing.

The problem posed by the present invention is to avoid the drawbacks of prior art systems, making it possible automatically and quickly to obtain the composition of a gas mixture being studied by light-emission spectroscopy, without requiring the intervention of an expert.

The invention thus seeks to make it possible to follow the variations in the composition of gas mixtures in real time.

The invention also seeks to automate interpreting the spectra obtained by light-emission spectroscopy apparatus.

For this purpose, the essential idea of the invention is to process the spectrum delivered by a light-emission spectrometer digitally and preferably in real time in order to extract meaningful information therefrom.

To do this, in the raw light-emission spectrum, it is considered that a steep slope is indicative of information that is useful for analyzing gaseous species. Thus, use is made of information in the spectrum that is identified as being in the vicinity of such a steeply sloping zone.

The spectrum is constituted by a plot of values for the intensity of light radiation as a function of the wavelength of the radiation. In practice, the results given by the optical spectrometer are contained in a set of tables, each table representing the spectrum at a sampling instant. Each table is made up of a sequence of intensity values and the simultaneous corresponding sequence of wavelength values.

The table is searched for zones that correspond to rapid variations in the intensity of light radiation as a function of wavelength. For each zone in the table corresponding to such rapid variation in the intensity of light radiation as a function of wavelength, the maximum intensity value in the vicinity of the zone of rapid intensity variation is identified, and the wavelength value corresponding to said intensity maximum is identified.

This defines a pruned optical spectrum table that contains only those maximum intensity values and the corresponding wavelength values that are in the immediate vicinity of zones in which intensity variation is greater than a determined threshold for intensity variation.

By means of this procedure, the raw optical spectrum, initially constituted by several thousands of points covering the spectral range of the spectrometer is simplified and replaced by a pruned optical spectrum containing only about one hundred characteristic points constituted by the maximum intensity values and the corresponding wavelengths for zones in which intensity variation is greater than the determined threshold.

The determined threshold for intensity variation can be adjusted depending on the extent to which it is desired to prune the spectrum.

In usual gas mixtures, a raw optical spectrum is a table made up of a sequence of several thousands of intensity values and of corresponding wavelength values. It will be understood that a comparison relating to such tables having several thousands of values is tedious and time consuming, making real time monitoring inconceivable.

SUMMARY OF THE INVENTION

Thus, to achieve these objects, and others, the invention provides a method of detecting gaseous species in a mixture by light-emission spectroscopy, in which use is made of the radiation emitted by a plasma present in the gas mixture under analysis, a measurement system is used to take a raw optical spectrum of said radiation emitted by the plasma, and the raw optical spectrum is compared with a library of reference optical spectra, the method comprising a step of generating a pruned optical spectrum, which step consists in making use, in the raw optical spectrum, of only those zones of the spectrum that present a significant shape corresponding to a predefined shape criterion, and subsequently said pruned spectrum is compared with the library of reference optical spectra.

The predefined shape criterion is preferably selected in such a manner as to reduce significantly the number of points representative of useful information contained in the spectrum, and thus the number of intensity values and corresponding wavelength values that need to be conserved in a table representing the spectrum.

In practice, the spectrum is processed reliably in particular by selecting as the predefined shape criterion the rate at which the amplitude of light radiation varies as a function of wavelength in the raw optical spectrum.

To do this, it is possible to proceed merely by making use, in the pruned optical spectrum, of the amplitude maximum values and the corresponding wavelength values in those zones of the raw optical spectrum that are adjacent to a zone in which the rate of amplitude variation is greater than a determined threshold rate.

The pruned optical spectrum then needs to be compared with reference optical spectra relating to the gaseous species likely to be present in the mixture under analysis.

Depending on the transmitted power, on the pressure, and on the nature of the gas mixture, a species will reach an excitation level that will enable it to emit at a well-defined wavelength. Scientific tables give most of the lines found by experiment or defined by quantum mechanics.

As a result, scientific tables for the spectra of gaseous species contain complete spectra, each characterized by a large amount of information, not all of which is necessarily present under the measurement conditions implemented on a given piece of equipment.

The invention seeks to take advantage of that observation in order to simplify the reference optical spectra as well.

To do this, a prior step is provided of establishing a library of reference optical spectra containing at least one reference optical spectrum for each gaseous species to be monitored, said reference optical spectrum being made by spectral analysis of the gaseous species to be monitored using said measurement system that is to be used for detecting gaseous species in the mixture, and said library of reference optical spectra is used for comparison with the pruned optical spectrum.

The advantage is that by making the reference optical spectrum using the said measurement system, a simplified spectrum is obtained which contains a smaller amount of characteristic data than do the spectra published in scientific tables, and the reference spectrum is adapted to the measurement conditions under which the invention is implemented. In particular, certain lines of the optical spectrum of the gaseous species under consideration may be missing, with such absences being the result of the real conditions under which the plasma is generated in the equipment containing said measurement system. The absence of such lines is thus not interpreted subsequently as a criterion indicating the absence of the corresponding gaseous species.

Thereafter, the invention proposes a step of pruning the reference optical spectrum, in the same manner as is done for the raw optical spectrum: during this step, in the pruned reference optical spectrum, use is made only of those amplitude maximum values and corresponding wavelength values that lie in zones of the reference optical spectrum that are adjacent to a zone in which the rate of amplitude variation is greater than a determined threshold rate for said reference optical spectrum. As a result, the pruned reference optical spectrum contains a significantly reduced number of characteristic values, and it corresponds to a data table of greatly reduced size.

It will then be understood that it is easier and faster to compare the pruned optical spectrum with reference optical spectra that are likewise pruned.

The invention also proposes extracting from the pruned optical spectrum that portion of the spectrum which corresponds to a gaseous species for monitoring, and then calculating the mean intensity value of the pruned optical spectrum for said gaseous species. It is then possible to identify and store or display the way in which it varies over time.

Because of its speed, the method of detecting gaseous species can find numerous applications in which gaseous species detection is implemented in real time, and in which warning or control signals can be generated as a function of the way in which said gaseous species vary.

In another aspect, the invention provides apparatus for implementing a method as defined above. Such apparatus comprises a plasma source for generating a plasma in the gas mixture under study, means for picking up and transmitting to an optical spectrometer the radiation emitted by the plasma, and a computer for analyzing the signals emitted by the optical spectrometer, the computer comprising a central unit and a program recorded in a program memory, said program including the sequence of instructions for implementing said method.

Preferably, the computer memory contains a library zone containing reference optical spectra for gaseous species to be analyzed.

BRIEF DESCRIPTION OF THE DRAWINGS

Other objects, characteristics, and advantages of the present invention appear from the following description of particular embodiments, given with reference to the accompanying figures, in which.

DETAILED DESCRIPTION OF THE INVENTION

Figure 1:
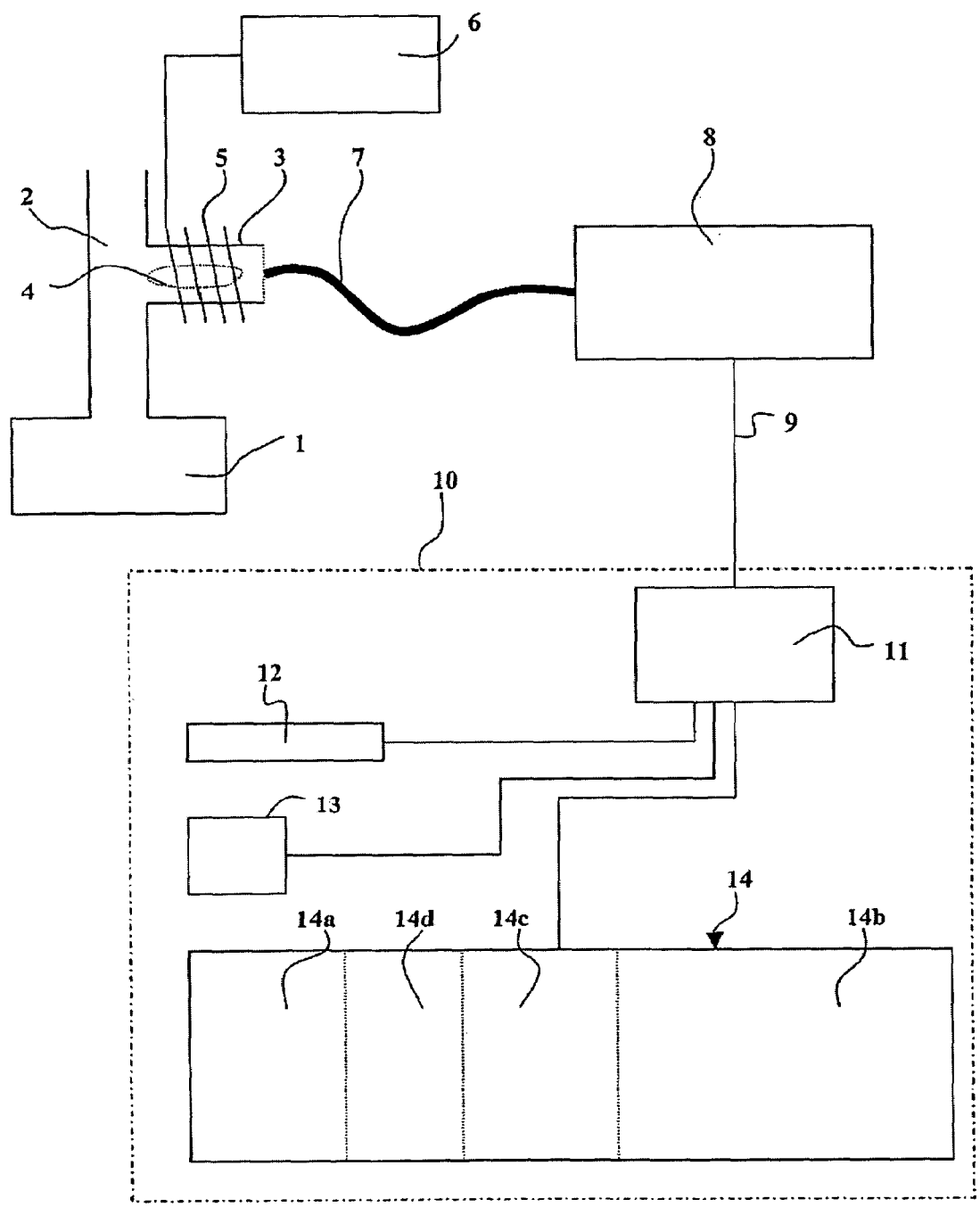
FIG. 1 is a diagram of a practical embodiment of apparatus of the present invention for detecting minority gaseous species.

In the embodiment shown in FIG. 1, the apparatus for detecting gaseous species in accordance with the invention is associated with equipment in which there flows a gas mixture for analysis. An example of such equipment comprises a process chamber 1 which could be constituted in non-limiting manner by a process chamber or a transfer chamber as used in the fabrication of semiconductors, or of micro-electromechanical systems (MEMS). However, the apparatus can also be applied to any other equipment in which it is desired to analyze a gas mixture.

In FIG. 1, the gas mixtures leave the vacuum chamber 1 via a vacuum pipe 2.

In the vacuum pipe 2, or in a branch excitation enclosure 3, or indeed in the vacuum chamber 1, there is a zone in which the gas mixture is excited to form a plasma 4. By way of example, in the branch excitation enclosure 3, a plasma 4 is made by electromagnetic excitation by means of an exciter antenna 5 powered by a power generator 6. Another example consists in using a microwave generator instead of the excitation antenna 5 fed by the power generator 6.

The light radiation emitted by the plasma 4 is picked up and transmitted to an optical spectrometer 8. Transmission may be performed by an optical fiber 7 or via a suitable connector, or via any other light transmission means.

The optical spectrometer 8 generates in known manner signals that constitute an image of the detected light spectrum, and sends them over a line 9 to a computer 10.

The computer 10 which is shown diagrammatically comprises a central unit 11 connected to input/output means 12 such as a keyboard, connected to display means 13 such as a screen, and connected to a memory 14.

The memory 14 contains a program zone 14a having programs recorded therein.

The memory 14 also contains a library zone 14b suitable for containing reference data.

The memory 14 contains a measurement memory zone 14c in which there can be recorded the data corresponding to raw light spectra received from the optical spectrometer 8.

The memory 14 contains a results memory zone 14d capable of containing pruned optical spectrum data obtained by processing raw optical spectra by the method of the invention.

The program zone 14a contains in particular a program for spectrum pruning using the method of the invention.

Figure 7:
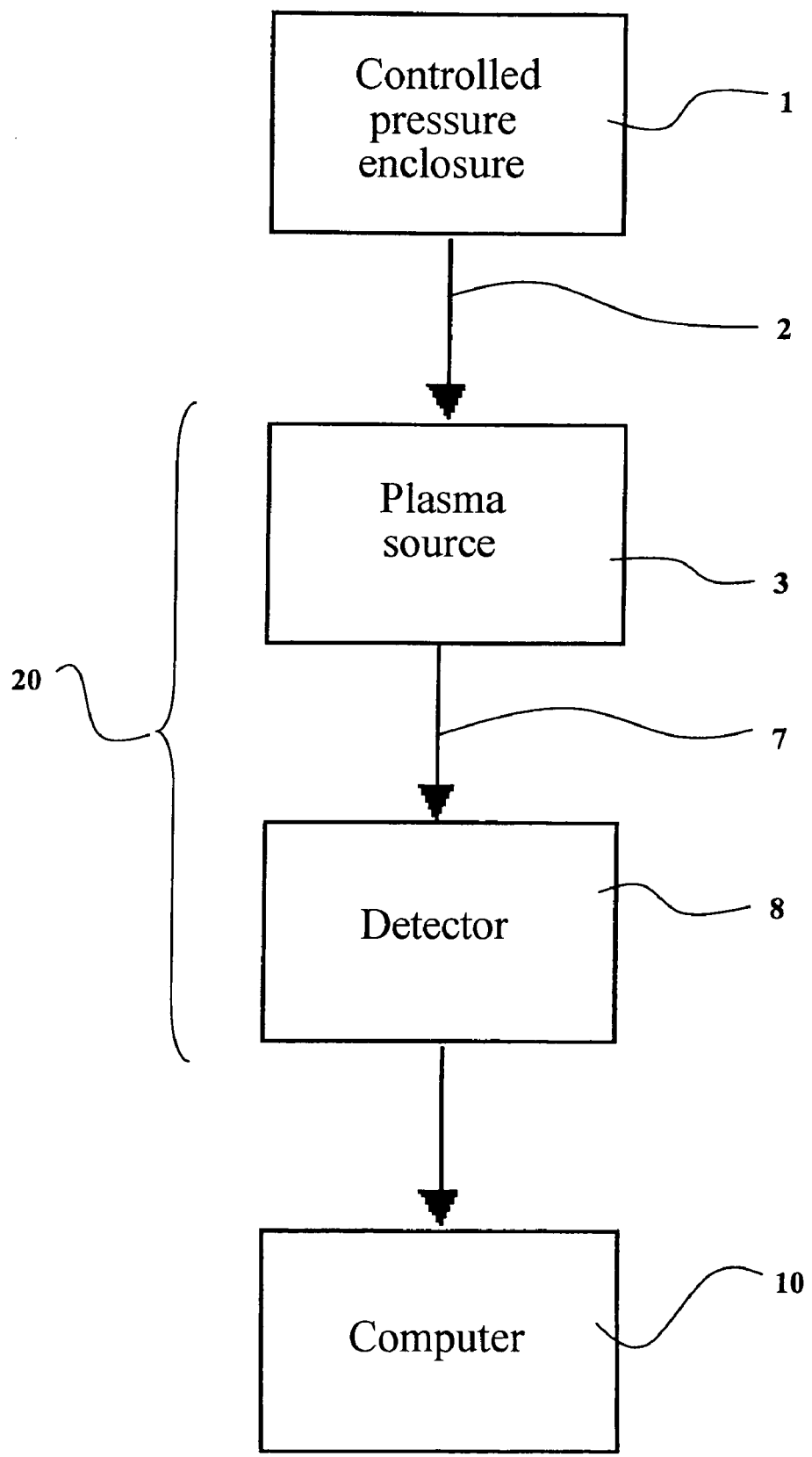
FIG. 7 is a diagram illustrating the location of the measurement system in the apparatus of FIG. 1.

The essential elements of the apparatus are reproduced diagrammatically in FIG. 7, where there can be seen the measurement system 20 constituted by the combination of the plasma source 3 and the light detector 8 such as an optical spectrometer.

Figure 2:
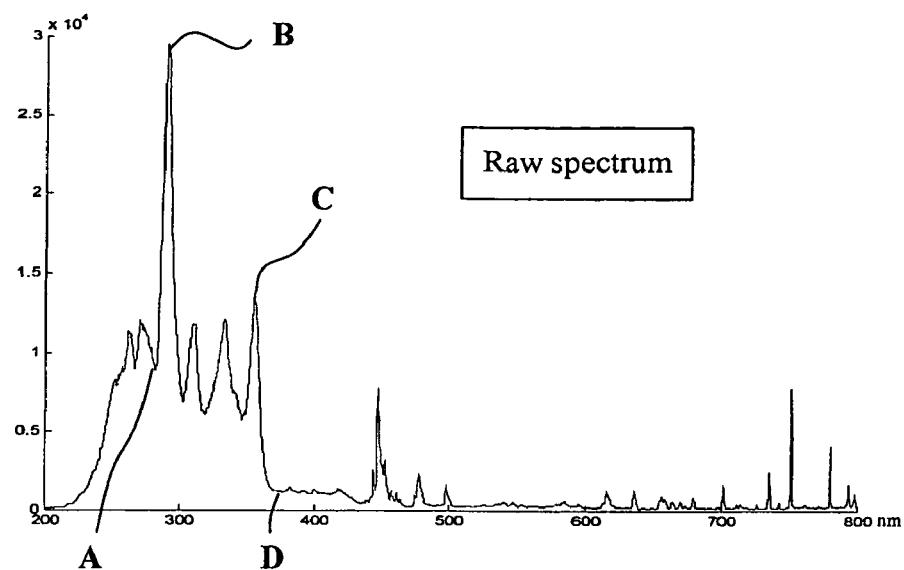
FIG. 2 is a light-emission spectrum of the kind that can be obtained from a light-emission spectrometer while analyzing a gas mixture, and taken by way of example.

The optical spectrum shown in FIG. 2 is considered below by way of example. FIG. 2 is a curve plotting light intensity up the ordinate as a function of wavelength along the abscissa. It can be seen that this curve, e.g. corresponding to a given gas mixture, has a large number of peaks or lines, i.e. zones forming maxima, and the same number of zones corresponding to minima, with some of the peaks being very steep, while others slope more gently.

By way of example, consider the portion of the curve going from point A to point B. In this portion of the curve, the rate at which light intensity varies as a function of wavelength is very high, since the slope of the curve is very great, the curve being almost vertical.

In contrast, in the zone situated between points C and D, the rate at which intensity varies as a function of wavelength is smaller than in the zone between points A to B.

This makes it possible, in the curve shown in FIG. 2, to define zones that present a high rate of variation in intensity as a function of wavelength, and zones that present a lower rate of variation in intensity as a function of wavelength.

In the spectrum of FIG. 2, if consideration is given essentially to peaks of large amplitude, a simplified spectrum can be made that contains only the amplitude values and the wavelength values corresponding to said peaks of large amplitude. However, such a simplified spectrum would be unsuitable for subsequently making a reliable comparison with spectra of pure gaseous species, and it is found that there is a large risk of error.

The invention avoids this risk of error by using a different method for pruning the spectrum.

In the invention, it is considered that the pertinent information in the spectrum lies in zones where the rate of variation in light intensity relative to wavelength is greater than a determined threshold.

Thus, use is made of light intensity and wavelength information in the spectrum of FIG. 2 when it lies in the vicinity of zones of the curve that present a slope greater than a determined threshold.

Figure 4:
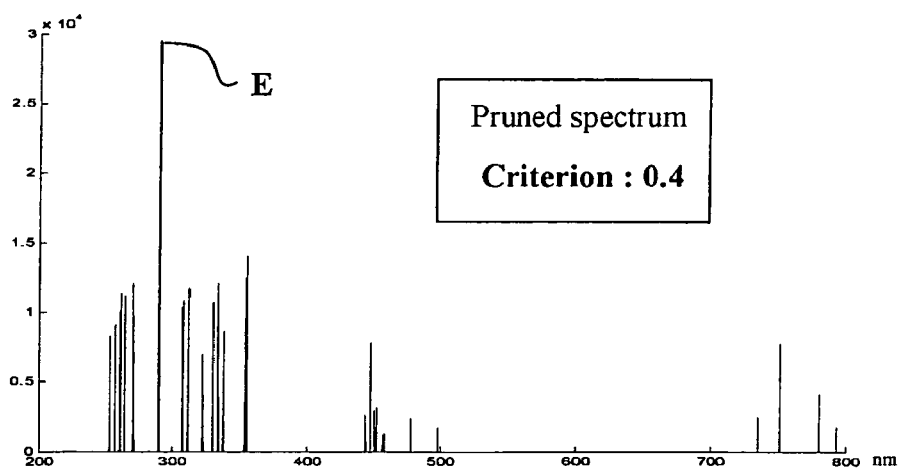
FIG. 4 shows the appearance of the pruned optical spectrum obtained from the spectrum of FIG. 2 by using a method of the invention in association with a first threshold rate for amplitude variation.
Figure 5:
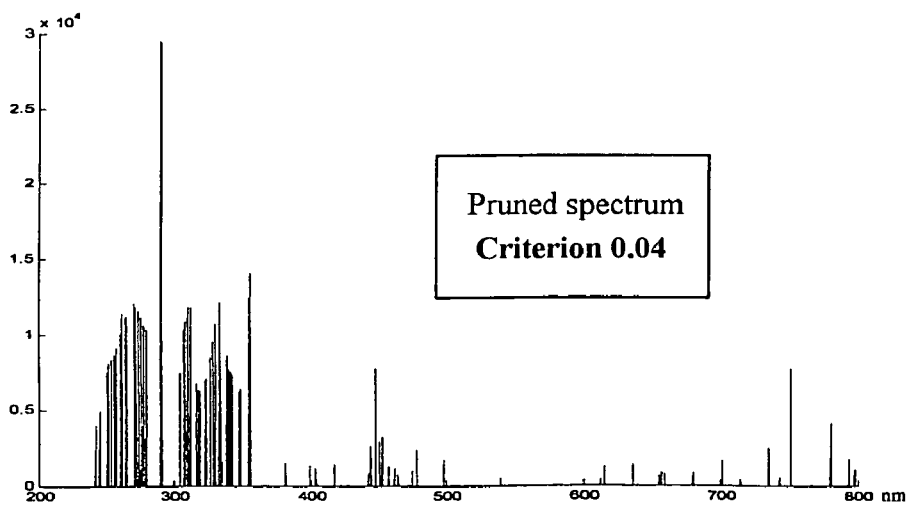
FIG. 5 shows the appearance of the pruned optical spectrum obtained from the spectrum of FIG. 2 by the method of the invention in association with a lower second threshold for the rate of amplitude variation.
Figure 3A:
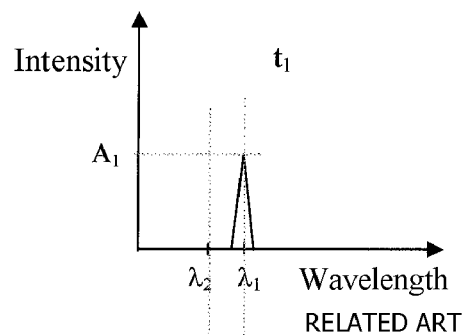
FIGS. 3A, 3B, and 3C show the difficulty of interpreting a spectrum of a mixture when using known software in association with spectrometers.
Figure 3B:
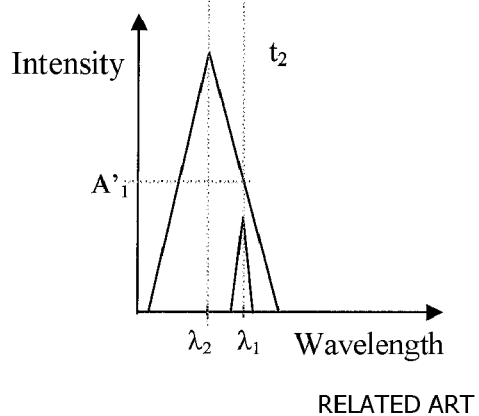
Figure 3C:
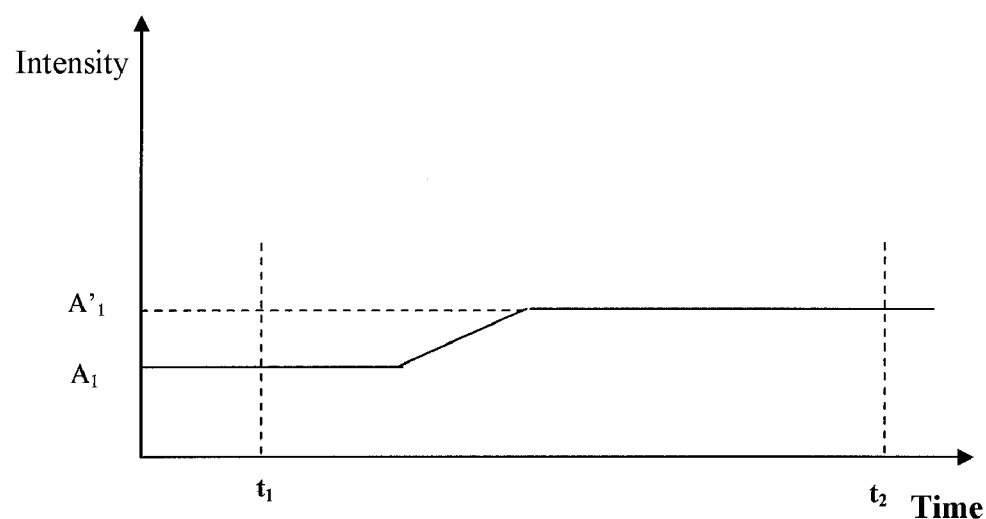

This leads to a pruned spectrum having the appearance as shown by way of example in FIG. 4 or 5.

The pruned spectrum is constituted by a sequence of pulses or disjoint vertical lines, of height corresponding to the peak intensity of the zone under consideration in the raw spectrum of FIG. 2. For example, a pulse E is to be found corresponding to the line of peak B that is visible in FIG. 2. The value of the pulse E corresponds to the light intensity of peak B, and it is situated at the wavelength of the peak B.

It can be seen that the pruned spectrum of FIG. 4 still contains the information relating to lines of large amplitude in the original raw spectrum of FIG. 2, for example information concerning the line of peak B.

However, it can be seen that the pruned spectrum of FIG. 4 also contains some information about lines of small amplitude, e.g. in the vicinity of wavelengths of 500 nanometers (nm) or 735 nm.

The pruned spectrum thus enables reliable analysis to be performed subsequently when it is compared with reference spectra for pure gaseous species.

There follows an illustration of the manner in which the person skilled in the art can select the rate of variation in the amplitude of light radiation as a function of wavelength in order to obtain a pruned spectrum that is sufficiently simple, but that still contains the essential information from the raw spectrum.

As mentioned above, the raw spectrum of FIG. 2 can be transformed into a pruned spectrum as shown in FIG. 4 by applying a shape criterion, i.e. a first threshold value for the rate of variation in the amplitude of light radiation as a function of wavelength. The criterion corresponds to the slope of the peak: the higher the criterion, the steeper the slope. The unit of the criterion is one light intensity unit per wavelength unit (nm). The light amplitude unit is associated with the light sensor used, so it is an arbitrary unit.

The value selected for this criterion depends on the shape of the spectrum. The value for the criterion will be smaller when a spectrum is already well defined by peaks having the appearance of Dirac pulses.

Thus, FIGS. 4 and 5 show respectively the result of pruning the spectra of FIG. 2 using a criterion of 0.4 and a criterion of 0.04. In FIG. 5, which was made using the smaller value criterion, it can be seen that the number of characteristic lines is greater than in FIG. 4 which was obtained using the larger-value criterion. It can thus be considered that a spectrum having a shape of the kind shown in FIG. 2 is advantageously pruned using a criterion of relatively low value, e.g. 0.04, in order to avoid losing too much information.

Figure 6A:
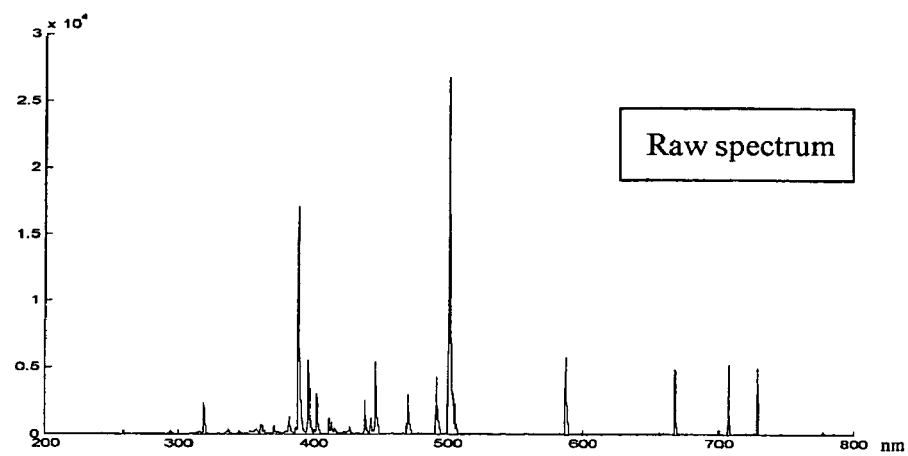
FIGS. 6A, 6B, and 6C show respectively another optical spectrum and the pruned optical spectra obtained by using the same first and second thresholds for rate of amplitude variation.
Figure 6B:
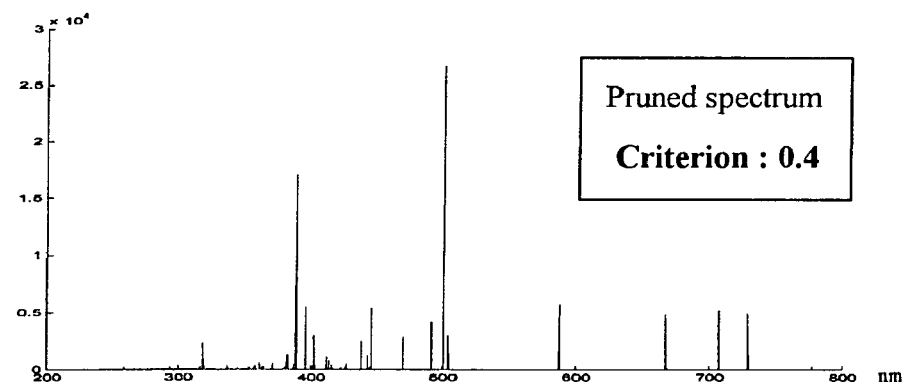
Figure 6C:
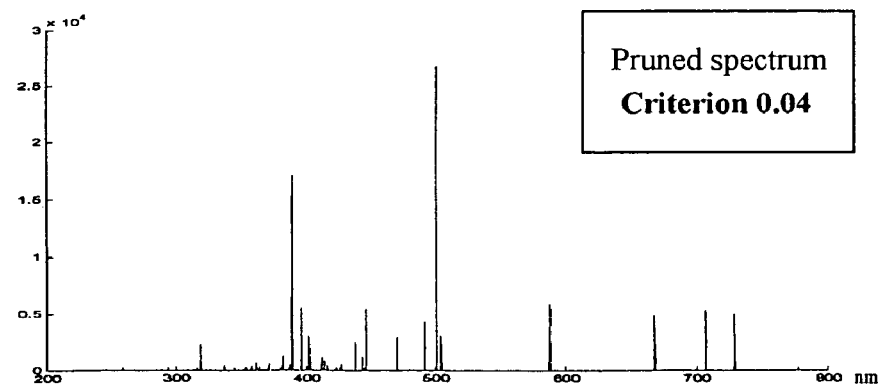

Consideration is now given to the spectra of FIGS. 6A, 6B, and 6C. FIGS. 6B and 6C show two pruned spectra using criteria having respective values of 0.4 and 0.04 and derived from the raw spectrum of FIG. 6A. In this case, it can be seen that the pruned spectra of FIGS. 6B and 6C are substantially identical, and that the spectrum of FIG. 6A is already in the form of very sharp peaks having the appearance of Dirac pulses. This shows that a spectrum of the type shown in FIG. 6A can be pruned by using a relatively high-value criterion, e.g. 0.4 as in FIG. 6B, and that there is no need to use a lower-value criterion, since pruning is already sufficient using a criterion of value 0.4.

The invention facilitates analysis of a raw optical spectrum as shown in FIG. 2 considerably, by replacing it with a pruned optical spectrum as shown in FIG. 4, which contains a smaller number of points and which can thus be converted into a table of values that is smaller in size.

Thereafter, it is also possible significantly to accelerate analyzing the optical spectrum by using the invention also to simplify and prune the reference optical spectra for each of the pure gaseous species that is to be found in the mixture.

To do this, the invention proposes implementing a prior training method using the measurement system 20 that is to be used for measurement purposes, in order to establish an internal library or reference spectra. The reference spectra may correspond to each pure gaseous species that it is desired to detect and monitor in the mixtures that are to be analyzed. Other reference spectra may correspond to mixtures of species that are to be monitored.

A library of reference spectra is thus established that is adapted to each light source and spectrometer pair making up a measurement system 20.

For this purpose, during the prior step, a pure gas for analysis is caused to flow through the measurement system 20 that is to be used subsequently, and the corresponding reference spectrum is stored. This spectrum contains the energy distribution of lines characteristic of the gaseous species as found under the same conditions as will apply subsequently when detecting the same gaseous species in a mixture for analysis. The library of spectra can thus be used as a database.

It should be observed that, for each gaseous species, this database contains only those lines that are likely to appear in the measurement system 20 that is actually used. Thus, compared with scientific tables, there is already a significant reduction in the volume of information that needs to be compared during analysis of the raw optical spectrum obtained for the gas mixture under analysis.

Thereafter, in the invention, a step is performed of pruning the spectrum for each gaseous species so as to further reduce the amount of information contained in the database, thereby further accelerating subsequent comparison between said information and the information in the pruned optical spectrum for the gas mixture under analysis.

When comparing the pruned optical spectrum with the library of pruned reference optical spectra as made in this way, some number of lines of the looked-for gaseous species will be found. Depending on the number of lines found in the spectrum under analysis, which may be evaluated as a percentage compared with the characteristic lines of the gas as input into the database, the software determines whether or not a gas is present. The pertinence of the result may be determined, for example, by the percentage of lines found. This criterion can be modified by the user.

Because it is possible to perform analysis in real time, due to the high speed with which it is possible to compare pruned spectra, the invention also makes it possible to monitor in real time the presence of a gaseous species in a mixture.

For this purpose, the software may calculate the mean intensity of light emission relating to a given gaseous species, i.e. the mean intensity value of the lines of the gaseous species in question in the pruned spectrum. This makes it possible to display variation in the single detected species, thus avoiding wrong interpretations for species that are difficult to observe.

It will be understood that the method of the invention, consisting in particular in pruning spectra, and in simplifying the spectrum library, greatly facilitates analysis of the spectra that are obtained, and makes it possible to automate said analysis and to accelerate it sufficiently to make it possible to perform analysis in real time, so as to monitor the variation in real time of gaseous species in a mixture.

Because of this speed, monitoring can serve to detect any change or departure relative to a previously determined normal state, by performing statistical processing on a population of measurements.

It is also possible to apply the technique to a plurality of pieces of equipment that operate in similar manner, and to make comparisons between them in order to detect possible defects on certain pieces of equipment.

To do this, a reference is initially established on one piece of equipment. The signatures as obtained in this way are then compared with the other pieces of equipment, thus making it possible to detect whether a parameter of such-and-such a piece of equipment has varied.

The method can be particularly useful after some action has been taken on a piece of equipment, for example after it has been put back into production. The data may also be associated with other data coming from that piece of equipment. The objective is to obtain a reference data population for that piece of equipment.

Thereafter, by monitoring the equipment in real time, it is possible to detect faults by statistical processing. The origin of a fault can then be interpreted in the light of signatures that have previously been identified for faults that have appeared in the past.

The advantage of the invention is that it makes it possible to obtain information about what is actually going on inside a piece of equipment, e.g. inside a process chamber, in contrast to that which can be achieved from the information available from the piece of equipment itself. It is possible to refine the signature of a particular piece of equipment by using new data taken in situ.

In practice, multiple applications can be found for the invention.

In a first example, it is possible to monitor the normal operating state of a piece of equipment through which there flows the gas mixture under analysis. To do this, gaseous species are selected for detection that are representative of the normal operating state of the equipment. Variation in real time of said selected gaseous species is monitored, and this variation is compared with reference variation data, and a warning or control signal is generated in the event of a departure from the reference variation data. One example lies in monitoring the leakage properties of the equipment. For leakproofing relative to the outside atmosphere, it is possible to look for moisture inside the equipment. For leakproofing between a plurality of chambers that might lead to transverse contamination, it is possible to look for any species that might be transferred from one chamber to another, depending on the processes concerned.

In a second example, the method of the invention is applied to monitoring a method being implemented in the equipment, e.g. in order to detect and/or control the end of some particular process. To do this, gaseous species are selected for detection that are representative of the state of progress of a process that makes use of the gas mixture under analysis; the variation of said selected gaseous species is monitored in real time and said variation is compared with reference variation data for the method, and a warning or control signal is generated in the event of departure from reference variation data for the process. An example may be controlling the end of etching semiconductor wafers by a fluorine etching process. Variation in the amplitude of a suitable line of fluorine is selected and monitored, and etching is interrupted when its amplitude reaches a threshold beyond which etching would be excessive. Tests have shown that the amplitudes of fluorine lines are representative of the state of progress of etching, and that these amplitudes increase regularly during etching.

In another example, the measurement method of the invention is applied to monitoring the effectiveness with which an enclosure is purged by purge gas. For this purpose, the gaseous species selected for detection are representative of the state of progress of a purging operation; the variation in said selected gaseous species is monitored in real time and said variation is compared with reference variation data for purging, and a warning or control signal is generated when the variation in the purged data reaches a state indicative of the end of purging, e.g. a threshold corresponding to the end of purging. For example, it is possible to monitor purging of an oven for depositing oxide by a low-pressure chemical vapor deposition (LPCVD) method that makes use of a precursor of tetraethoxysilane (TEOS) ($C_8H_{20}O_4Si$). A search is then made in the nitrogen for traces of Si, O, CO, CN, N, this list not being exhaustive.

In another example, the detection method of the invention, applies to monitoring the purity of a gas. Under such circumstances, the gas mixture is a gas whose purity is to be monitored. For example, the mean value for the amplitudes of lines in the pruned spectrum corresponding to the gas to be monitored is compared with the mean value for the amplitudes of the lines in the pruned spectrum for other gaseous species present in the mixture, and the degree of purity of the gas is deduced from said comparison.

In another example, the method of the invention for detecting gaseous species is applied to detecting the end of a chamber being reconditioned. Under such circumstances, gaseous species are selected that are representative of the reconditioning state of a chamber being reconditioned; the real time variation in said selected gaseous species in said chamber being reconditioned is monitored, and said variation is compared with a given threshold or with reference variation data for chamber reconditioning, and a warning or control signal is generated when the data for said selected gaseous species reaches a state indicative of the end of chamber reconditioning, e.g. when a predetermined threshold is reached.

For example, when reconditioning process chambers used in semiconductor fabrication technology, it is possible to detect species of interest, namely chlorine or fluorine, and it is considered that a chamber has been reconditioned once the levels at which chlorine and fluorine are present have become stable. Such a detection method makes it possible significantly to accelerate the reconditioning procedure, by avoiding pointlessly lengthening the steps of chamber reconditioning.

The present invention is not restricted to the implementations described explicitly above, but it includes the various generalizations and variants that are within the competence of the person skilled in the art.

What is claimed is:

1. A method of detecting gaseous species in a mixture by light-emission spectroscopy, in which use is made of the radiation emitted by a plasma present in the gas mixture under analysis, a measurement system is used to take a raw optical spectrum of said radiation emitted by the plasma, and the raw optical spectrum is compared with a library of reference optical spectra, the method comprising:
generating a pruned optical spectrum, including making use, in the raw optical spectrum, of only those zones of the spectrum that present a significant shape corresponding to a predefined shape criterion of said gaseous species in said mixture, and
subsequently comparing said pruned spectrum with the library of reference optical spectra, and determining the presence of gaseous species based on the comparing, wherein said detecting of said gaseous species is implemented in real-time.

2. A method according to claim 1, in which the predefined shape criterion is the rate at which the amplitude of the light radiation varies as a function of wavelength in the raw optical spectrum.

3. A method according to claim 2, in which the maximum amplitude values and the corresponding wavelength values are taken from the pruned optical spectrum from zones of the raw optical spectrum that are adjacent to a zone in which the rate of amplitude variation is greater than a predetermined threshold rate.

4. A method according to claim 1, including a prior step of establishing a library of reference optical spectra including at least one reference optical spectrum for each gaseous species to be monitored, said reference optical spectrum being obtained by spectral analysis of the gaseous species to be monitored using said measurement system that is to be used for detecting gaseous species in the mixture, and said library of reference optical spectra is used for comparison with the pruned optical spectrum.

5. A method according to claim 4, in which establishing each reference optical spectrum includes a step of pruning the reference optical spectrum, during which step use is made of the maximum amplitude values and the corresponding wavelength values that are located in a pruned reference optical spectrum in zones of the reference optical spectrum that are adjacent to a zone in which the rate of amplitude variation is greater than a determined threshold rate in said reference optical spectrum.

6. A method according to claim 1, in which the portion of the spectrum corresponding to a gaseous species to be monitored is extracted from the pruned optical spectrum, the mean intensity value of the pruned optical spectrum of said gaseous species is calculated, and variation thereof over time is identified and stored or displayed.

7. A method according to claim 1, in which the gaseous species for detection are selected so as to be representative of the operating state of said piece of equipment through which the gas mixture under analysis flows, variation in said selected gaseous species is monitored in real time, said variation is compared with reference variation data, and a warning or control signal is generated on departure from the reference variation data.

8. A method according to claim 1, in which gaseous species for detection are selected that are representative of the state of progress of a process implementing the gas mixture under analysis, variation in said selected gaseous species is monitored in real time, said variation is compared with reference variation data for the method, and a warning or control signal is generated on departure from the reference variation data for the process.

9. A method according to claim 1, in which gaseous species for detection are selected that are representative of the state of progress of the purging of an enclosure by a purge gas which is detected, variation in real time of said selected gaseous species is monitored, said variation is compared with reference variation data for purging, and a warning or control signal is generated when the variation data for purging reaches a state indicative of the end of purging.

10. A method according to claim 1, in which the gas mixture is a gas whose purity is to be monitored, the mean value of the pruned spectrum corresponding to the gas being monitored is compared with the mean values of the pruned spectra for other gaseous species present in the mixture.

11. A method according to claim 1, in which gaseous species are selected that are representative of the state of reconditioning of a chamber being reconditioned, variation in said selected gaseous species in said chamber being reconditioned is monitored in real time, said variation is compared with reference variation data for chamber reconditioning, and a warning or control signal is generated when the data for said selected gaseous species reaches a state indicative of the end of chamber reconditioning.

12. Apparatus for implementing a method of detecting gaseous species in a mixture by light-emission spectroscopy, in which use is made of the radiation emitted by a plasma present in the gas mixture under analysis, a measurement system is used to take a raw optical spectrum of said radiation emitted by the plasma, and the raw optical spectrum is compared with a library of reference optical spectra, the apparatus comprising;

a plasma source for generating a plasma in the gas mixture under study, means for picking up and transmitting to an optical spectrometer the radiation emitted by the plasma, a computer for analyzing the signals emitted by the optical spectrometer, the computer comprising a central unit and a program recorded in a program memory, said program containing the sequence of instructions for implementing said method, wherein said method includes the steps of:

generating a pruned optical spectrum, including making use, in the raw optical spectrum, of only those zones of the spectrum that present a significant shape corresponding to a predefined shape criterion of said gaseous species in said mixture, and subsequently comparing said pruned spectrum with the library of reference optical spectra, and determining the presence of gaseous species based on the comparing, wherein said detecting of said gaseous species is implemented in real-time.

13. Apparatus according to claim 12, in which the memory of the computer contains a library zone containing the reference optical spectra of the gaseous species to be analyzed.

* * * * *